United States Patent [19]
Weber et al.

[11] 4,094,984
[45] June 13, 1978

[54] 6-PHENYL-8-BROMO-4H-S-TRIAZOLO-[3,4C]-THIENO-[2,3E]-1,4-DIAZEPINES AND SALTS THEREOF

[75] Inventors: Karl-Heinz Weber, Gau-Algesheim; Adolf Baüer, Ingelheim am Rhein; Peter Danneberg, Ockenheim; Franz Josef Kühn, Bingen, all of Germany

[73] Assignee: Boehringer Ingelheim GmbH, Ingelheim am Rhein, Germany

[21] Appl. No.: 839,792

[22] Filed: Oct. 6, 1977

Related U.S. Application Data

[63] Continuation of Ser. No. 672,280, Mar. 31, 1976, abandoned, which is a continuation-in-part of Ser. No. 554,309, Feb. 28, 1975, abandoned.

[30] Foreign Application Priority Data

| Mar. 2, 1974 | Germany | 2410030 |
| Jul. 20, 1974 | Germany | 2435041 |
| Sep. 24, 1974 | Germany | 2445430 |
| Dec. 21, 1974 | Germany | 2460776 |

[51] Int. Cl.² ............ A61K 31/55; C07D 495/04; C07D 495/14
[52] U.S. Cl. ............ 424/269; 260/239.3 B; 260/308 R; 260/332.2 R; 260/332.3 R; 260/332.3 P; 260/332.5
[58] Field of Search ............ 260/308 R; 424/269

[56] References Cited

U.S. PATENT DOCUMENTS

| 3,681,343 | 8/1972 | Hester | 260/308 R |
| 3,904,641 | 9/1975 | Nakanishi et al. | 260/308 R |
| 3,952,006 | 4/1976 | Tahara et al. | 260/308 R |

FOREIGN PATENT DOCUMENTS

| 2,405,682 | 8/1974 | Germany | 260/308 R |

OTHER PUBLICATIONS

Araki et al., Chem. Abstracts, vol. 82, Abstract No. 171102(g), (1975).

*Primary Examiner*—Alton D. Rollins
*Attorney, Agent, or Firm*—Hammond & Littell

[57] ABSTRACT

Compounds of the formula

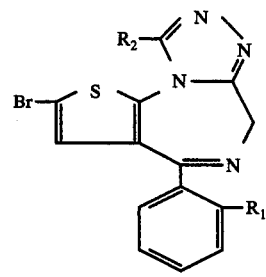

wherein $R_1$ is hydrogen, fluorine, chlorine, bromine, nitro or trifluoromethyl; and $R_2$ is hydrogen, alkyl of 1 to 4 carbon atoms or hydroxyalkyl of 1 to 4 carbon atoms; and non-toxic, pharmacologically acceptable acid addition salts thereof; the compounds as well as their salts are useful as tranquilizers, muscle-relaxants and anticonvulsants.

8 Claims, No Drawings

6-PHENYL-8-BROMO-4H-S-TRIAZOLO-[3,4C]-THIENO-[2,3E]-1,4-DIAZEPINES AND SALTS THEREOF

This is a continuation of Ser. No. 672,280, filed Mar. 31, 1976, now abandoned, which is a continuation-in-part of copending application Ser. No. 554,309 filed Feb. 28, 1975, now abandoned.

This invention relates to novel 6-phenyl-8-bromo-4H-s-triazolo-[3,4c]-thieno-[2,3e]-1,4-diazepines and non-toxic acid addition salts thereof, as well as to methods of preparing these compounds.

More particularly, the present application relates to a novel class of compounds represented by the formula

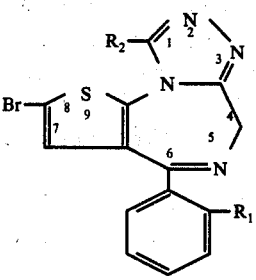
(I)

wherein $R_1$ is hydrogen, fluorine, chlorine, bromine, nitro or trifluoromethyl; and $R_2$ is hydrogen, alkyl of 1 to 4 carbon atoms or hydroxyalkyl of 1 to 4 carbon atoms; and non-toxic, pharmacologically acceptable acid addition salts thereof.

The compounds embraced by formula I above may be prepared by the following methods:

METHOD A

By reacting a compound of the formula

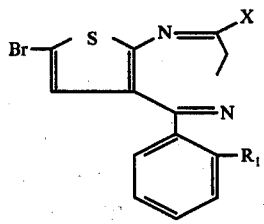
(II)

wherein R has the meanings previously defined, and X is SH—, NH$_2$—, lower alkoxy, lower alkylmercapto- or halogen, with a compound of the formula

$R_2$—CO—NH—NH$_2$ (III)

wherein $R_2$ has the meanings previously defined.

METHOD B

By reacting a compound of the formula

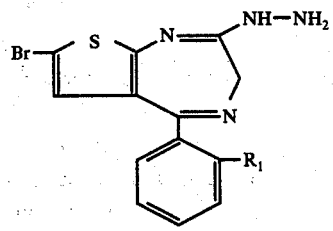
(IV)

wherein $R_1$ has the meanings previously defined, with an acid of the formula $R_2$—COOH (V)

wherein $R_2$ has the meanings defined above, or with a functional derivative of this acid.

The reaction described under method A may be carried out at temperatures between 100° and 250° C without a solvent as well as with a solvent, such as methanol, ethanol, dioxane, chloroform, tetrahydrofuran, benzene, toluene, xylene or mixtures of any two or more of these, and in the presence or absence of an acid catalyst, such as hydrochloric acid, sulfuric acid, phosphoric acid, polyphosphoric acid, acetic acid, propionic acid, benzenesulfonic acid or toluene-sulfonic acid; it is generally allowed to proceed to the end product without isolating the intermediate product of the formula

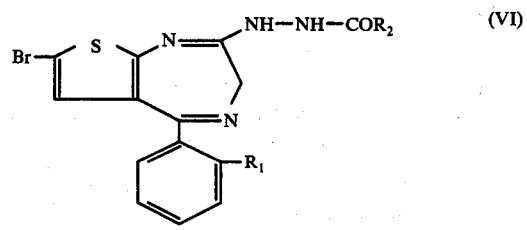
(VI)

wherein $R_1$ and $R_2$ have the meanings previously defined, but under milder reaction conditions (for instance, at room temperature) it is possible to isolate the intermediate product without difficulties.

The reaction described under method B proceeds with the free acid of the formula V or with a suitable functional derivative of this acid. Examples of suitable functional derivatives of the acid of the formula V are an orthoester of the formula $R_2$-C(OR')$_3$; an iminoether of the formula $R_2$—C(=NH)—OR; an amidine of the formula $R_2$—C—(=NH)—NH$_2$; an amide of the formula $R_2$—CONH$_2$; a thioamide of the formula $R_2$—CSNH$_2$; an ester of the formula $R_2$—COOR" (for example, a methyl, ethyl or nitrophenyl ester); an acid anhydride of the formula $R_2$—CO)$_2$O; an acid halide of the formula $R_2$—COHal; or a nitrile of the formula $R_2$—CN; in these formulas $R_2$ has the meanings previously defined, R' is lower alkyl, and R" is aliphatic, araliphatic or aromatic hydrocarbyl. The iminoethers and amidines are used in the form of their salts formed with mineral acids, e.g. as their chlorohydrates, as conventional.

The reaction conditions may be chosen pursuant to the particular acid derivative which is used. Generally, the reaction may be carried out without a solvent or with a solvent, (such as in methanol, ethanol, chloroform, tetrahydrofuran, benzene, toluene or mixtures of any two or more of these, without or in the presence of an acid catalyst, such as hydrochloric acid, sulfuric acid, phosphoric acid, polyphosphoric acid, acetic acid, propionic acid, benzenesulfonic acid or toluenesulfonic acid. The presence of a base, such as 2-methylimidazole, as catalyst is useful as well. The reaction temperature lies between 0° and 300° C, preferably 20° to 180° C.

The following further describe the particular variants of this method:

VARIANT I

In this case the functional derivative of the acid of the formula V is an orthoester of the formula $R_2-C(OR')_3$ where $R_2$ and $R'$ have the meanings defined above. Usually, the reaction proceeds in the presence of an excess of the orthoester which serves simultaneously as the solvent medium, at temperatures between 90° and 100° C; or one of the aforementioned solvents, optionally in the presence of one of the aforementioned catalysts, at temperatures between room temperature and the reflux temperature of the reaction mixture.

VARIANT II

In this case the functional derivative of the acid of the formula V is an iminoether of the formula $R_2-C(=NH)-OR'$, where $R_2$ and $R'$ have the previously defined meanings. It is advantageous to perform the reaction in one of the previously mentioned solvents at a temperature between room temperature and the reflux temperature of the reaction mixture.

VARIANT III

In this case the functional derivative of acid of the formula V is an amidine of the formula $R_2-C(=NH)-NH_2$, where $R_2$ has the meaning previously defined. It is advantageous to perform the reaction in the presence of a basic catalyst, such as 2-methylimidazole, at elevated temperatures, for example between 150° and 250° C. In case the reaction temperature is lower, for example if the reaction is carried out at room temperature, an intermediate product of the formula

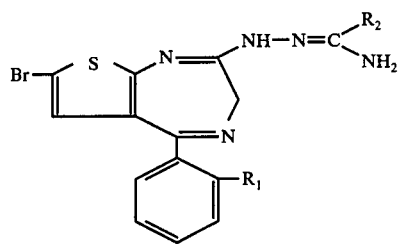

(VII)

where $R_1$ and $R_2$ have the previously defined meanings, is first formed. This intermediate product may be isolated and subsequently subjected to a cyclization reaction by heating it at 150° to 250° C. However, isolation is not required by any means.

VARIANT IV

In this case the functional derivative of the acid of the formula V is an amide or thioamide of the formula $R_2$-$CONH_2$ or $R_2$-$CSNH_2$, where $R_2$ has the meanings defined above. The reaction may be performed with or without a solvent, and without or with catalyst, at temperatures between 0° and 300° C.

VARIANT V

Here, the functional derivative of acid of the formula V is an ester of the formula $R_2$-COOR", an anhydride of the formula $(R_2CO)_2O$, an acid halide of the formula $R_2$—COHal, or a nitrile of the formula $R_2$—CN, where $R_2$ and R" have the previously defined meanings. At first, the intermediate product of the formula VI is formed, which is then cyclized as indicated under method A.

The end products of the formula I form acid addition salts with inorganic or organic acids. Examples of non-toxic, pharmacologically acceptable acid addition salts are those formed with hydrohalic acids, sulfuric acid, phosphoric acid, nitric acid, cyclohexylsulfaminic acid, citric acid, tartaric acid, ascorbic acid, maleic acid, formic acid, salicylic acid, methane- or toluene-sulfonic acid, 8-chlorotheophylline or the like.

The starting compounds of the formulas III and V are described in the literature, and the preparation of the compounds of the formulas VI and VII is described above.

The hydrazine derivatives of the formula IV may be prepared by reacting a compound of the formula II with hydrazine. This reaction may be performed in one of the above-mentioned solvents and, if desired, in the presence of one of the previously mentioned acid catalysts, advantageously at a temperature between room temperature and the reflux temperature of the reaction mixture.

The compounds of the formula II, which may be reacted either directly with compounds of the formula III to form compounds of the formula I, or else may be reacted with hydrazine to form compounds of the formula IV, are prepared starting from known (see German Offenlegungsschrift No. 2,217,157) compounds of the formula

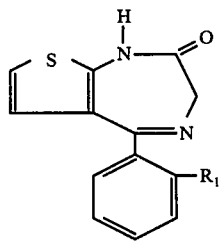

(VIII)

wherein $R_1$ has the previously defined meanings, by brominating them in conventional manner, and reacting the resulting compounds of the formula

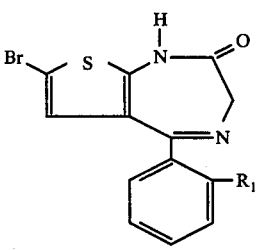

(IX)

wherein $R_1$ has the previously defined meanings, in a solvent, such as pyridine, dimethylformamide or tetrahydrofuran or mixtures thereof. The reaction temperature may lie between room temperature and the reflux temperature of the reaction mixture. In this manner the compounds of the formula II wherein X is —SH are obtained. They exist in tautomeric equilibrium with the corresponding thiono compounds, as follows:

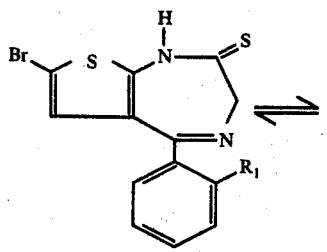

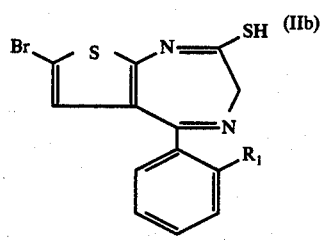

wherein $R_1$ has the previously defined meanings. These compounds may, after they have been converted into the corresponding salts by reaction with a metallizing agent, such as sodium methylate or sodium amide in a solvent, be reacted without previous isolation with alkylating agents, such as methyl iodide or another lower alkyl iodide to form those compounds of the formula II wherein X is lower alkylthio.

Compounds of the formulas VIII and IX may be obtained pursuant to the methods of German Offenlegungsschrift Nos. 2,107,356 and 2,144,105, namely by subjecting compounds of the formula

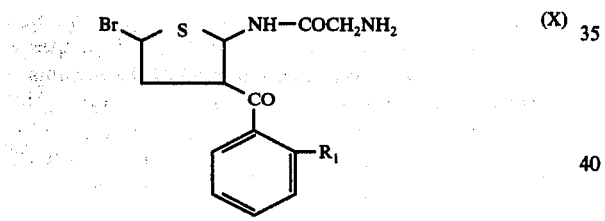

wherein $R_1$ has the previously defined meanings, to intramolecular condensation. An especially advantageous variant of this reaction consists of effecting the cyclization by boiling in toluene in a vessel provided with a water trap, using silicagel as the dehydrating agent. In this matter significantly higher yields and purer products are obtained.

Compounds of the formula II, wherein X is lower alkoxy, may be obtained by reacting known aminoketones of the formula

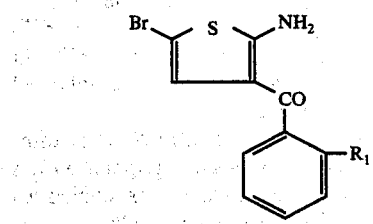

wherein $R_1$ has the previously defined meanings, with a halo-orthoacetate of the formula

wherein R' has the previously defined meanings and Hal is chlorine, bromine or iodine, to form a compound of the formula

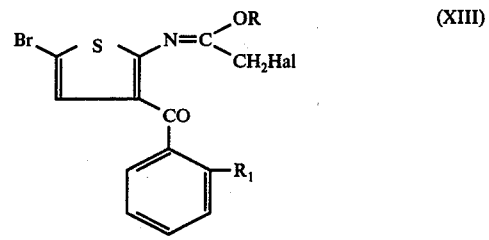

wherein R, $R_1$ and Hal have the previously defined meanings. In those instances where Hal is chlorine, it is advantageous first to exchange the aliphatically bonded chlorine atom in the compound of the formula XIII for iodine by means of the Finkelstein Reaction, for example by reacting it with sodium iodine in acetone. Then, the iodo-substituted compound thus obtained is reacted with ammonia in dioxane or tetrahydrofuran. In this manner, an intermediate amino compound of the formula

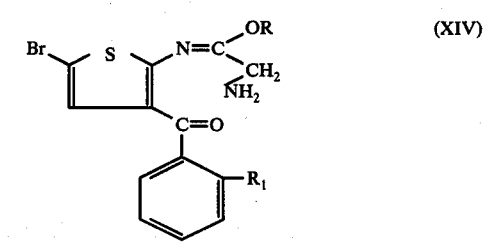

wherein R, $R_1$ and $R_2$ have the previously defined meanings, is formed which, however, cyclizes spontaneously into a compound of the formula

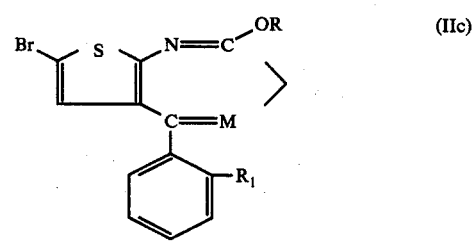

wherein R and $R_1$ have the previously defined meanings.

Compounds of the formula II, wherein X is amino, may be prepared by reacting compounds of the formula IX, which were obtained by halogenation of compounds of the formula VIII, with ammonia. The reaction is advantageously performed in a solvent, such as tetrahydrofuran, and in the presence of a Lewis acid, such as titanium chloride, for example.

These compounds also exist in tautomeric equilibrium as follows:

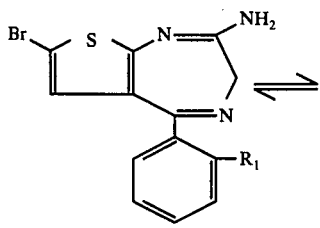

(IId)

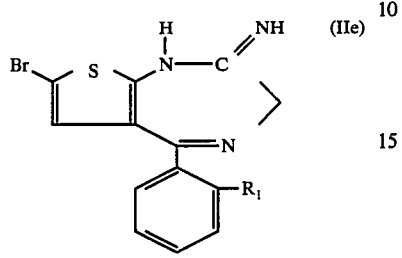

(IIe)

wherein $R_1$ has the previously defined meanings.

The following examples illustrate the present invention and will enable others skilled in the art to understand it more completely. It should be understood, however, that the invention is not limited solely to the particular examples given below.

EXAMPLE 1

8-Bromo-6-(o-chloro-phenyl)-1-methyl-4H-s-triazolo-[3,4c]-thieno-[2,3e]-1,4-diazepine (a) 11.5 gm of 7-bromo-5-(o-chloro-phenyl)-3H-[2,3e]-thieno-1,4-diazepin-2-one (see German Offenlegungsschrift 2,221,623), i.e. a compound of the formula IX, were heated at 55°–60° C with 100 cc of absolute pyridine and 6.5 gm of phosphorus pentasulfide for 4 hours while stirring. The mixture was allowed to cool and was then poured into 100 cc of saturated ice-cold NaCl-solution. The precipitate was collected by suction filtration, washed with water, dissolved in 100 cc of methylene chloride, the solution was dried and evaporated, and the residue was treated with a little methylene chloride. After suction filtration, 6 gm of brown crystalline 7-bromo-5-(o-chloro-phenyl)-3H-[2,3e]-thieno-1,4-diazepine-2-thione, a compound of the formula IIa, m.p. 214° C (decomp.) were obtained.

(b) 6.0 gm of this compound were suspended in 100 cc of tetrahydrofuran, and the suspension was stirred at room temperature with 1.2 gm of hydrazine hydrate for 20 minutes. After evaporation to about 10 cc, 20 cc of ether were added, and the crystals were collected by suction filtration. Yield: 5.2 gm of 7-bromo-5-(o-chloro-phenyl)-2-hydrazino-3-H-[2,3e]-thieno-1,4-diazepine, m.p. ~ 300° C (decomp.), a compound of the formula IV.

(c) 5.2 gm of this compound were suspended in 50 cc of orthotriethyl acetate, and the suspension was heated to 80° C. After about 30 minutes a clear solution was first formed from which later colorless crystals separated out. The mixture was allowed to cool, and the crystals were collected by suction filtration and washed with ether. Yield: 5 gm of the compound, m.p. 211°–213° C, of the formula

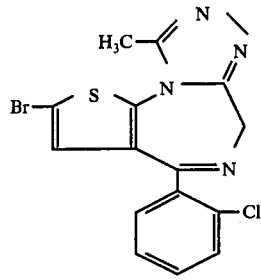

EXAMPLE 2

8-Bromo-6-(o-chloro-phenyl)-1-hydroxyethyl-4H-s-triazolo-[3,4c]-thieno-[2,3e]-1,4-diazepine 4.8 gm of 7-bromo-5-(o-chloro-phenyl)-3H-[2,3e]-thieno-1,4-diazepine-2-thione [see Example 1(a)] were heated together with 3.4 gm of glycolic acid hydrazide in 100 cc of n-butanol in an $N_2$-atmosphere until the mixture boiled, and then it was refluxed for 5 hours, whereupon it was partially evaporated, and the compound named in the heading was caused to crystallize out by addition of isopropyl ether. The product, m.p. 224°–226° C, was obtained with a yield of 60% of theory.

The starting compounds of formula IX were obtained as follows:

(a) Similar to the example described in German Offenlegungsschrift No. 2,221,623, 0.03 mol of a compound of the formula VIII were dissolved or suspended in 60 cc of chloroform and, after addition of 6cc of pyridine, admixed with 4.7 gm of bromine, in the course of 5 minutes. Stirring was continued for 45 minutes at 25°–30° C, whereupon the compound of the formula X separated out, mostly as a yellow precipitate, which was collected by suction filtration and washed with ether. 10 to 12 gm of the compound of the formula IX were obtained. It may be used for thionization as the crude product.

(b) 17 gm of the 2-bromoacetylamino-3-[aryl]-thiophene thus obtained were dissolved in 200 to 250 cc of chloroform and admixed at room temperature with 20 cc of pyridine, followed by addition of 5 cc of bromine. After 2 hours' stirring, the mixture was shaken several times with water, the chloroform phase was dried with $MgSO_4$ and evaporated, and the residue stirred with isoether. Yield: 10 to 15 gm of a 2-bromoacetylamino-3-[aryl]-4-bromothiophene.

10 gm of this compound were dissolved in 400 cc of ethylacetate, and over a period of 2 hours gaseous ammonia was introduced into the solution at room temperature. The precipitated ammonium chloride was separated by suction filtration, the filtrate was evaporated in vacuo, and 7 to 8 gm of an aminoacylamino compound of the formula X was obtained.

7 gm of this compound were boiled in 80 cc of toluene and 25 gm of silicagel in a vessel equipped with a water trap for 1 hour. The mixture was cooled to 50°–60° C, and 50 cc of methanol were added. After suction filtration and washing, 3 to 4 gm of the desired compound of the formula IX were obtained from the filtrate.

The preparation of the starting compounds of the formula II is illustrated by the following:

0.2 mol of 2-amino-5-bromo-3-(o-chloro-benzoyl)thiophene, a compound of the formula XI, was boiled, while stirring, with 78.4 gm (0.4 mol) of orthoethylchloro-acetate (see formula XII) in one liter of benzene for 8 hours; after about 4 hours of boiling 0.01 ml of trifluoro-acetic acid was added. The solvent was then evaporated, and the unreacted orthoester was removed by high-vacuum distillation.

The raw product thus obtained was stirred in 1.5 liters of acetone with 16 to 20 gm of sodium iodide for 6 hours at room temperature. The mixture was then evaporated, and the residue was taken up in methylene chloride. The methylene chloride solution was extracted with ice water several times and dried with magnesium sulfate.

The residue (the corresponding crude product of the formula XIII) was taken up in 150 cc of absolute dioxane, and ammonia gas was introduced over a period of 1 to 2 hours at room temperature. Then, the solvent was removed in vacuo, the residue was taken up in methylene chloride, and the solution was washed with ice water, dried with magnesium sulfate and evaporated. The remaining oil was identified to be the desired compound and may be reacted, as described above, analogous to the thio compound, into the hydrazino derivative.

Using the above-described methods, the following additional compounds of the formula I were prepared:

| Example No. | $R_1$ | $R_2$ | $R_3$ | M.P. °C |
|---|---|---|---|---|
| 3 | Br | Br | $CH_3$ | 205 – 206 |
| 4 | Br | F | $CH_3$ | 210 |
| 5 | Br | H | $CH_3$ | 284 |
| 6 | Br | Cl | H | 216 – 218 |
| 7 | Br | Cl | $iC_3H_7$ | 203 – 205 |

The compounds of this invention, that is, those embraced by formula I above and their non-toxic, pharmacologically acceptable acid addition salts, have useful pharmacodynamic properties. More particularly, they exhibit anxiety-relieving (anxiolytic), tension-relieving, muscle-relaxing and very effective anticonvulsive activities in warm-blooded animals, such as mice and rats. They also increase the food-intake in mammals. The compounds of this invention, moreover, are characterized by extraordinarily low toxicity.

In the so-called pentetrazole-antagonism test for anticonvulsive activity the compounds of the present invention have been found to be far superior to the thieno-1,4-diazepines disclosed in German Offenlegungsschrift No. 2,155,403 and 2,221,623; and while the compounds of this invention exhibit an activity picture similar to that of the 8-alkyl-6-aryl-thieno-[2,3e]-4H-s-triazolo-[3,4c]-1,4-diazepines disclosed in German Offenlegungsschrift No. 2,229,845, the former's intensity of activity is more than ten times that of the latter's.

Particularly effective are those compounds of the formula I wherein $R_1$ is chlorine or bromine, and $R_2$ is methyl, and their non-toxic acid addition salts. The following are specific examples of such particularly effective compounds: 8-bromo-6-o-chloro-phenyl-1-methyl-4H-s-triazolo-[3,4c]-thieno-[2,3e]-1,4-diazepine ($R_1$=Cl, $R_2$=$CH_3$); and 8-bromo-6-o-bromo-phenyl-1-methyl-4H-s-triazolo-[3,4c]-thieno-[2,3e]-1,4-diazepine ($R_1$=Br, $R_2$=$CH_3$);

The above-indicated pharmacodynamic properties of the compounds of this invention were ascertained by means of various standard test methods, namely the following:

1. *Pentetrazole antagonisim* [M. I. Gluckmann, Curr. Ther. Res. 7, 721 (1965)]. The median effective dose ($ED_{50}$) of the test compound is determined which cancels the lethal effect of 125 mgm/kg of pentylenetetrazole in 50% of the test animals; the pentylenetetrazole is administered intraperitoneally one hour after administration of the test compound.

2. *Electroshock* [J. E. P. Tomann et al, J. NeuroPhysiol. 9, 231 (1946)].

3. *Conflicting Situation* (Inhibition of Passive Avoidance Test) [J. Geller, Arch. Int. Pharmacodyn. 149,243 (1964)].

4. *Fighting Test* (Suppression of isolation-induced aggressiveness in mice) [Wirth et al; Arch. Int. Pharmcodyn. 115, 1–31 (1958)].

5. *Toxicity* [Litchfield and Wilcoxon, J. Pharmacol. Exp. Therap. 96, 99(1949)]. Determination of median lethal dose ($LD_{50}$).

Albino mice (NMRI) having a body weight of 20 to 25 gm or albino rats (FW-49) having a body weight of 140 to 200 gm were used as the test animals, and the test compounds were administered perorally as a suspension in olive oil by means of an esophageal sound.

The following table shows the results (values graphically determined) obtained from test No. 1, i.e. the pentetrazole antagonism test, for a representative number of compounds of the formula I as well as for analogous compounds disclosed in German Offenlegungsschrift No. 2,405,682, namely:

Compounds of this invention
A = 8-Bromo-6-(o-chlorophenyl)-1-methyl-4H-s-triazolo [3,4c]thieno[2,3e]1,4-diazepine
B = 8-Bromo-6-(o-fluorophenyl)-1-methyl-4H-s-triazolo[3,4c]thieno[2,3e]1,4-diazepine
C = 8-Bromo-6-(o-bromophenyl)-1-methyl-4H-s-triazolo[3,4c]thieno[2,33]1,4-diazepine
D = 8-bromo-6-phenyl-1-methyl-4H-s-triazolo[3,4]-thieno[2,3e]1,4-diazepine
Compounds of the German publication
E = 8-Ethyl-6-(o-chlorophenyl)-1-methyl-4H-s-triazolo[3,4c]thieno[2,3e]-1,4-diazepine
F = 8-Chloro-6-(o-chlorophenyl)-1-methyl-4H-s-triazolo[3,4c]thieno[2,3e]1,4-diazepine
G = 8-Chloro-6-(o-bromophenyl)-1-methyl-4H-s-triazolo[3,4c]thieno[2,3e]1,4-diazepine
H = 8-Chloro-6-phenyl-1-methyl-4H-s-triazolo[3,4c]-thieno[2,3e]1,4-diazepine

| Compound | Pentylenetetrazole antagonism Mouse $ED_{50}$ mg/kg p.o. | $LD_{50}$ Mouse mg/kg p.o. | Therap. Index. $LD_{50}$:$ED_{50}$ Mouse p.o. |
|---|---|---|---|
| A | 0.07 | >3,500 | >50,000 |
| B | 0.15 | >3,300 | >22,000 |
| C | 0.12 | >3,500 | >29,166 |
| D | 0.8 | | |
| E | 0.7 | 3,070 | 4,386 |
| F | 1.0 | 2,300 | 2,300 |
| G | 0.7 | 2,200 | 3,143 |
| H | 3.0 | | |

The results tabulated above clearly show that in each case the 8-bromo-substituted compound according to the present invention is significantly more effective and strikingly less toxic than the corresponding 8-ethyl- or 8-chloro-substituted compound of the German publication.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 0.84 mgm/kg body weight, preferably 0.016 to 0.42 mgm/kg body weight (oral). The daily dose rate is 0.083 to 2.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 8

Tablets

The tablet composition is compounded from the following ingredients:

| | |
|---|---|
| 8-Bromo-6-(o-chloro-phenyl)-1-methyl -4H-s-triazolo[3,4c]-thieno-[2,3e]- 1,4-diazepine | 0.5 parts |
| Lactose | 50.0 parts |
| Corn starch | 43.5 parts |
| Soluble starch | 5.0 parts |
| Magnesium stearate | 1.0 parts |
| Total | 100.0 parts |

Preparation:

The triazolo-thieno-diazepine compound and the magnesium stearate are admixed with each other, the mixture is moistened with an aqueous solution of the soluble starch, the moist mass is granulated through a 1 mm-mesh screen, the granulate is dried and again passed through the screen, and the dry granulate is intimately admixed with the lactose and the corn starch. The resulting composition is compressed into 100 mg-tablets, each of which contains 0.5 mgm of the triazolo-thieno-diazepine compound and is an oral dosage unit composition with effective anxiolytic, tension-relieving, muscle-relaxing and anticonvulsive action.

EXAMPLE 9

Coated pills

The pill core composition is compounded from the following ingredients:

| | |
|---|---|
| 8-Bromo-6-(o-bromo-phenyl)-1-methyl -4H-s-triazolo-[3,4c]-thieno-[2,3e]- 1,4-diazepine | 1.0 parts |
| Lactose | 28.5 parts |
| Corn starch | 19.0 parts |
| Gelatin | 1.0 parts |
| Magnesium stearate | 0.5 parts |
| Total | 50.0 parts |

Preparation:

The triazolo-thieno-diazepine compound, the lactose and the corn starch are intimately admixed with each other, the mixture is granulated through a 1 mm-mesh screen with the aid of an aqueous 10% solution of the gelatin, the granulate is dried and again passed through the screen, and the dry granulate is admixed with the magnesium stearate. The resulting composition is compressed into 50 mgm-pill cores which are subsequently coated with a thin shell consisting essentially of a mixture of sugar, titanium dioxide, talcum and gum arabic, and finally polished with beeswax. Each coated pill contains 1 mgm of the triazolo-thieno-diazepine compound and is an oral dosage unit composition with effective anxiolytic, tension-relieving, muscle-relaxing and anticonvulsive action.

EXAMPLE 10

Suppositories

The suppository composition is compounded from the following ingredients:

| | |
|---|---|
| 8-Bromo-6-(o-chloro-phenyl)-1-hydroxymethyl -4H-s-triazolo-[3,4c]-thieno-[2,3e]-1,4- diazepine | 5.0 parts |
| Suppository base (e.g. cocoa butter) | 1695.0 parts |
| Total | 1700.0 parts |

Preparation:

The suppository base is melted and cooled to 40° C, the finely pulverized triazolo-thien-diazepine compound is stirred into the suppository base with the aid of an immersion homogenizer, and 1700 mgm-portions of the resulting mixture at 35° C are poured into cooled suppository molds and allowed to harden therein. Each suppository contains 5 mgm of the thiazolo-thieno-diazepine compound and is a rectal dosage unit composition with effective anxiolytic, tension-relieving, muscle-relaxing and anticonvulsive action.

Analogous results are obtained when any one of the other triazolo-benzodiazepinones embraced by formula I or a non-toxic, pharmacologically acceptable acid addition salt thereof was substituted for the particular triazolo-thienodiazepine in Examples 8 through 10. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

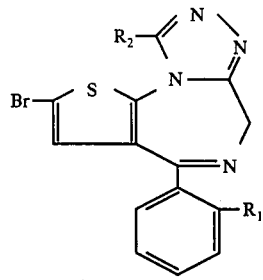

wherein $R_1$ is hydrogen, fluorine, chlorine, bromine, nitro or trifluoromethyl; and $R_2$ is hydrogen, alkyl of 1 to 4 carbon atoms or hydroalkyl of 1 to 4 carbon atoms; or a non-toxic, pharmacologically acceptable acid addition salt thereof.

2. A compound of claim 1, where $R_1$ is chlorine or bromine, and $R_2$ is methyl or a non-toxic, pharmacologically acceptable acid addition salt thereof.

3. A compound of claim 2, which is 8-bromo-6-(o-chloro-phenyl)-1-methyl-4H-s-triazolo-[3,4c]-thieno-[2,3e]-1,4-diazepine or a non-toxic, pharmacologically acceptable acid addition salt thereof.

4. A compound of claim 2, which is 8-bromo-6-(o-bromo-phenyl)-1-methyl-4H-s-triazolo-[3,4c]-thieno-[2,33]-1,4-diazepine or a non-toxic, pharmacologically acceptable acid addition salt thereof.

5. A compound of claim 2, which is 8-bromo-6-(o-fluoro-phenyl)-1-methyl-4H-s-triazolo-[3,4c]-thieno-[2,33]-1,4-diazepine or a non-toxic, pharmacologically acceptable acid addition salt thereof.

6. A compound of claim 2, which is 8-bromo-6-(o-chloro-phenyl)-1-hydroxyethyl-4H-s-triazolo-[3,4c]-thieno[2,3e]-1,4-diazepine or a non-toxic, pharmacologically acceptable acid addition salt thereof.

7. A pharmaceutical dosage unit composition consisting essentially of an inert pharmaceutical carrier and an effective anxiolytic, tension-relieving, muscle-relaxing or anticonvulsive amount of a compound of claim 1.

8. The method of relieving anxiety, relieving tension, relaxing the muscles or suppressing convulsions in a warm-blooded animal, which comprises perorally, parenterally or rectally administering to said animal an effective anxiolytic, tension-relieving, muscle relaxing or anticonvulsive amount of a compound of claim 1.

* * * * *

UNITED STATES PATENT OFFICE
CERTIFICATE OF CORRECTION

Patent No. 4,094,984           Dated June 13, 1978

Inventor(s) KARL HEINZ WEBER, ADOLF BAUER, PETER DANNEBERG and JOSEF KÜHN

It is certified that error appears in the above-identified patent and that said Letters Patent are hereby corrected as shown below:

Col. 1, line 49, correct "R has" to read

--$R_1$ has-- .

Col. 2, line 46, correct "$R_2$-CO)$_2$O" to read

--$(R_2$-CO$)_2$O--

Col. 5, lines 33 to 43, correct the formula to read

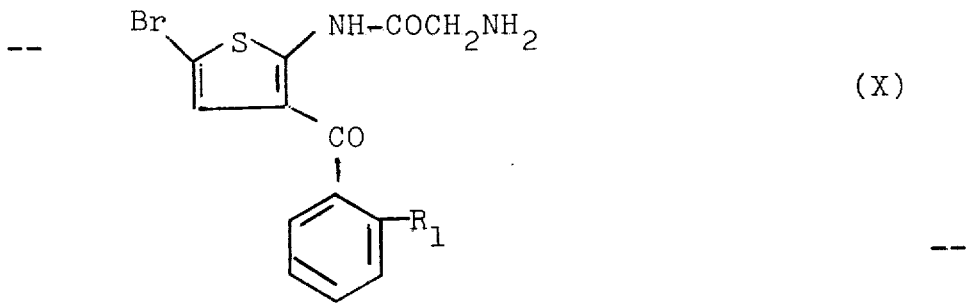

(X)

Col. 6, lines 45 to 54, correct the formula to read

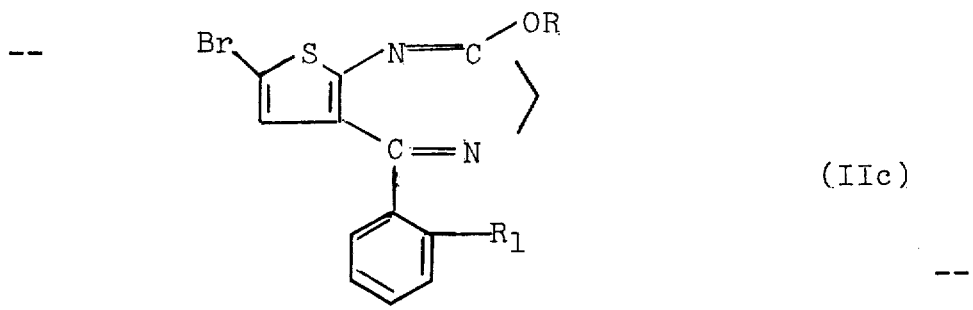

(IIc)

UNITED STATES PATENT OFFICE
CERTIFICATE OF CORRECTION

Patent No. 4,094,984     Dated June 13, 1978

Inventor(s) KARL HEINZ WEBER, ADOLF BAUER, PETER DANNEBERG and JOSEPH KÜHN

It is certified that error appears in the above-identified patent and that said Letters Patent are hereby corrected as shown below:

Col. 10, line 39, correct "[2,33]" to read

--[2,3e]--.

Col. 13, line 18, correct "[2,33]" to read

--[2,3e]--.

Col. 14, line 3, correct "[2,33]" to read

--[2,3e]--.

Signed and Sealed this

Fourteenth Day of November 1978

[SEAL]

Attest:

RUTH C. MASON
Attesting Officer

DONALD W. BANNER
Commissioner of Patents and Trademarks